United States Patent
Li et al.

(10) Patent No.: US 9,861,289 B2
(45) Date of Patent: *Jan. 9, 2018

(54) COMPLIANT WEARABLE PATCH CAPABLE OF MEASURING ELECTRICAL SIGNALS

(71) Applicant: VivaLnk Limited (Cayman Islands), Santa Clara, CA (US)

(72) Inventors: Jiang Li, Cupertino, CA (US); Junfeng Mei, Sunnyvale, CA (US); Zhigang Wang, Fremont, CA (US)

(73) Assignee: VivaLnk, Inc., Santa Clara, CA (US)

( * ) Notice: Subject to any disclaimer, the term of this patent is extended or adjusted under 35 U.S.C. 154(b) by 701 days.

This patent is subject to a terminal disclaimer.

(21) Appl. No.: 14/520,674

(22) Filed: Oct. 22, 2014

(65) Prior Publication Data

US 2016/0113544 A1    Apr. 28, 2016

(51) Int. Cl.
| | |
|---|---|
| A61B 5/0408 | (2006.01) |
| A61B 5/00 | (2006.01) |
| A61B 5/0478 | (2006.01) |
| A61B 5/0492 | (2006.01) |

(52) U.S. Cl.
CPC .......... *A61B 5/0408* (2013.01); *A61B 5/0006* (2013.01); *A61B 5/0478* (2013.01); *A61B 5/04085* (2013.01); *A61B 5/0492* (2013.01); *A61B 5/6833* (2013.01); *A61B 5/002* (2013.01); *A61B 5/0024* (2013.01); *A61B 2560/0412* (2013.01); *A61B 2562/0209* (2013.01);
(Continued)

(58) Field of Classification Search
CPC . A61B 5/04087; A61B 5/6833; A61B 5/0478; A61B 5/0006; A61B 5/04; A61B 5/0492; A61B 5/0531; A61B 2562/164; A61B 5/04085; A61B 5/0024; A61B 5/002; A61B 2562/125; A61B 2562/209; A61B 2560/0412
USPC ........................................................ 606/391
See application file for complete search history.

(56) References Cited

U.S. PATENT DOCUMENTS

| | | | | |
|---|---|---|---|---|
| 5,305,746 A | * | 4/1994 | Fendrock | A61B 5/0408 600/391 |
| 5,370,115 A | * | 12/1994 | Ogawa | A61B 5/0408 600/372 |

(Continued)

OTHER PUBLICATIONS

Kanyanta, Valentine., Ivankovic, Alojz., Mechanical Characterization of Polyurethane Elastomer for Biomedical Applications. 2010. Journal of the Mechanical Behavior of Biomedical Materials, 3 (1): 51-62.*

*Primary Examiner* — Lee S Cohen
*Assistant Examiner* — Eunhwa Kim
(74) *Attorney, Agent, or Firm* — SV Patent Service (57) ABSTRACT

A wearable patch capable of wireless communications includes an elastic layer, an adhesive layer under the elastic layer, and a shearable electrode layer that includes: a support substrate comprising one or more openings so positioned to allow the shearable electrode layer to be sheared and elongated, and breathable, an upper electrode layer on the support substrate, and a lower electrode layer under the support substrate. The support substrate can include a via that is conductively connected to the upper electrode layer and the lower electrode layer. The lower electrode can be in contact with a user's body and to pick up electric signals from the user's body.

16 Claims, 6 Drawing Sheets

(52) U.S. Cl.
CPC ... *A61B 2562/125* (2013.01); *A61B 2562/164* (2013.01); *A61B 2562/166* (2013.01)

(56) References Cited

U.S. PATENT DOCUMENTS

| | | | | |
|---|---|---|---|---|
| 7,245,957 | B2 * | 7/2007 | Rowe | A61B 5/0408 600/391 |
| 8,165,655 | B2 * | 4/2012 | Grassi | A61N 1/0408 600/391 |
| 2007/0270672 | A1 | 11/2007 | Hayter | |
| 2009/0171180 | A1 | 7/2009 | Pering | |
| 2011/0237921 | A1 * | 9/2011 | Askin, III | A61B 5/0408 600/377 |
| 2012/0242481 | A1 | 9/2012 | Gernandt | |
| 2013/0041235 | A1 * | 2/2013 | Rogers | A61B 5/6867 600/306 |

* cited by examiner

COMPLIANT WEARABLE PATCH CAPABLE OF MEASURING ELECTRICAL SIGNALS

BACKGROUND OF THE INVENTION

The present application relates to wearable wireless electronic devices, and in particular, to tag-like or patch-like wireless devices that can adhere to human skin.

Wearable patches or tags can communicate with smart phones and other devices using WiFi, Bluetooth, or NFC technologies. Near Field Communication (NFC) is a wireless communication standard which enables two devices in a short range to establish a communication channel within a short period of time through radio waves in the 13.56 MHz frequency range. NFC can be a useful technology for data transfer between two devices in close proximity to one another. Because it needs the two devices to be in close proximity to one another (less than 10 cm), it is more secure than other wireless technologies like Bluetooth and Wi-Fi. Hence, it can be seen as an easy and secure tool for establishing quick two-way connections for data transfer. NFC is a two-way communication tool, one of the devices/cards can have a passive NFC tag that can reduce the cost and still behave in the same way as any other RFID tag. NFC uses passive energy that is collected through active electromagnetic coupling from the reader devices, so it brings another benefit of these NFC tags do not need a battery in its system that simplify the product design and make disposable product possible.

This communication standard is being increasingly adopted for use in wireless transactions, including money transfer, loyalty coupons, gift cards, transit passes, tickets, etc. Mobile handset manufacturing companies are increasingly integrating NFC hardware in their phones. For example, the 2014 CES badges employed NFC technology and have resulted in shorter lines, more badge functionality, and greater ease of use for attendees and exhibitors. NFC has also been increasingly used in the fields of medical devices, electronic health records, as well as wearable tagging devices.

In other scenarios, long communication distance is required, such as >10 meters. Without tapping the reader device in the close range NFC patch from time to time, data can be collected automatically and continuously with least operator interference. In such cases, Bluetooth and WiFi are a proper option with a 1.5V or 3V battery supply.

Wearable tag (or patch) is an electronic tag that can be worn by a user. Wearable patch is required to directly stay on user's skin and function for an extended period of time from hours to months. A wearable patch can contain a micro-electronic system and can be accessed using NFC, Bluethooth, WiFi, or other wireless technologies. For example, an authentication wearable tag can be used to recognize a user's smart phone for authentication purpose. It can also be integrated with different sensors for other purposes such as vital signs monitoring, motion track, skin temperature measurements and ECG detection.

Despite initial development efforts, conventional wearable devices still face several drawbacks: they may not provide adequate comfort for users to wear them; they may not stay attached to user's body for the required length of time; they are usually not aesthetically appealing.

Another drawback of conventional wearable patches is that the rigid polymer substrate does not allow much breathability to the skin. The build-up of sweat and moisture can cause discomfort and irritation to the skin, especially after wearing it for an extended period of time. In addition, their rigid substrates are very difficult to conform to curved surfaces.

Moreover, conventional wearable devices are often not robust enough to sustain repeated elongations during the movements of the body that the wearable patches are attached to. Under stress, different layers in wearable patches can break or delaminate rendering the patches inoperable.

On the other hand, conventional electrodes for measuring human organ electrical activities are usually bulky and not stretchable or flexible. The data collection process is usually at the cost of life quality for users.

There is therefore a need for a device for measuring human organs' electrical signals which are durable and comfortable for users to wear.

SUMMARY OF THE INVENTION

The presently disclosure attempts to address the aforementioned limitations in conventional wearable patches. The disclosed wearable patches are highly compliant and flexible, while also being able to support the circuit, chips, and other electronic components in the wearable patch. The disclosed wearable patches can change their physical shape and dimension to relieve stresses such as repeated elongations, therefore increasing durability of the wearable patches as well as provide comfort to the user. The disclosed wearable patches can stay attached to skin for long period of time even enduring muscle movements underneath the skin to provide constant contact to the skin and comfort to the user.

Furthermore, the disclosed wearable patches can include thin, flexible and stretchable electrodes that are configured for measuring human organ electrical activities such as ECG, EEG, EMG, etc. The disclosed wearable patches are capable of measuring electrical signals in human body and are very stretchable, flexible, breathable, and comfortable to use.

Furthermore, the disclosed wearable patches are aesthetically appealing.

In one general aspect, the present invention relates to a wearable patch, comprising: an elastic layer; an adhesive layer under the elastic layer; and a shearable electrode layer, comprising: a support substrate comprising one or more openings so positioned to allow the shearable electrode layer to be sheared and elongated, and breathable; an upper electrode layer on the support substrate; and a lower electrode layer under the support substrate, wherein the support substrate includes a via that is conductively connected to the upper electrode layer and the lower electrode layer, wherein the lower electrode is configured to be in contact with a user's body and to pick up electric signals from the user's body.

Implementations of the system may include one or more of the following. The elastic layer and the adhesive layer respectively can include registered openings which expose an upper surface of the upper electrode layer. The registered openings can allow an electric lead to connect the upper electrode layer to an external device. The elastic layer and the adhesive layer can be wider than the shearable electrode layer. The elastic layer and the adhesive layer can be wider than the shearable electrode layer by an edge clearance along an edge, wherein the edge clearance has a width between 0.5 mm and 100 mm. The support substrate can have a Young's Modulus higher than 0.5 Gpa. The support substrate can be thinner than 1.0 mm. The elastic layer can have a Young's Modulus lower than 0.3 Gpa.

In another general aspect, the present invention relates to a wearable patch capable of wireless communications, comprising: an elastic layer; an adhesive layer under the elastic layer; and a shearable electrode layer, comprising: a first circuit module comprising: a first support substrate; a conductive circuit embedded in the first support substrate; and a semiconductor chip in connection with the conductive circuit; and a second circuit module comprising: a second support substrate comprising one or more openings to allow the shearable electrode layer to be sheared and elongated, and breathable; an upper electrode layer on the second support substrate; and a lower electrode layer under the second support substrate, wherein the second support substrate includes a via that is conductively connected to the upper electrode layer and the lower electrode layer, wherein the lower electrode is configured to be in contact with a user's body and to pick up electric signals from the user's body; and flexible ribbons that connect the first support substrate in the first circuit module and the second support substrate in the second circuit module, wherein the flexible ribbon is embedded with a connecting line configured to transmit the electrical signal from the upper electrode layer to the first circuit module.

Implementations of the system may include one or more of the following. The first circuit module is configured to receive or transmit wireless signals in communications with an external device. The conductive circuit can include an antenna circuit configured to receive or transmit wireless signals in communications with an external device. The first circuit module can wirelessly communicate with the external device based on near field communication (NFC), Wi-Fi, Bluetooth, or RFID wireless communication standard. The support substrate can have a Young's Modulus higher than 0.5 Gpa. The support substrate can be thinner than 0.5 mm. The elastic layer can have a Young's Modulus lower than 0.3 Gpa. At least one of the flexible ribbons can include a polymer matrix; and a conductive trace layer embedded in the polymer matrix, wherein the conductive trace layer has a zigzag structure, wherein the conductive trace layer is configured to connect the conductive circuit in the first circuit module and the upper electrode layer the second circuit module.

In another general aspect, the present invention relates to a wearable patch capable of wireless communications, comprising: an elastomer matrix comprising a lower surface; a first circuit module in the elastomer matrix comprising: a conductive circuit; and a semiconductor chip in connection with the conductive circuit; and a second circuit module in the elastomer matrix comprising: an upper electrode layer on the second support substrate; and a lower electrode layer configured to be in contact with a user's skin and to pick up electric signals from the user's body; and a via through the elastomer matrix and configured to conductively connect the upper electrode layer and the lower electrode layer; flexible ribbons in the elastomer matrix and configured to connect the first circuit module and the second circuit module, wherein the flexible ribbon includes a connecting line configured to transmit the electrical signal from the upper electrode layer to the first circuit module; and an adhesive layer on the lower surface of the elastomer matrix layer.

Implementations of the system may include one or more of the following. The elastomer matrix can include one or more openings to allow the wearable patch to be sheared and elongated, and breathable for the user's skin.

These and other aspects, their implementations and other features are described in detail in the drawings, the description and the claims.

DETAILED DESCRIPTION OF THE INVENTION

Figure 1:
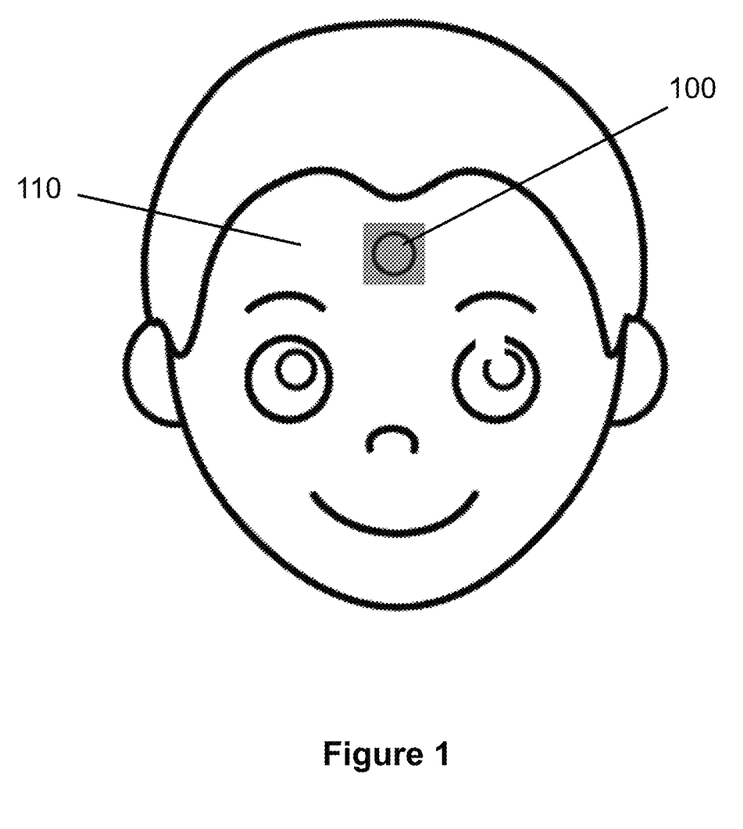
FIG. 1 illustrates the usage of a compliant wearable patch that is attached to a user's skin.

Referring to FIG. 1, a compliant wearable patch 100 can be placed on and adheres to a person's skin 110 on his or her body such as forehead, hand, wrist, arm, shoulder, breast, waist, leg, foot, etc.

As discussed above, there are several challenges for wearable patches on human skin. The patches need to stay on skin for an extended period enduring various daily activities such as taking showers or bathes, swimming, exercises, holding weights, etc. The patches also need to adapt their physical dimension to adhere to the skin, which will change its shape by the muscle movements underneath. The patches are also rubbed by clothing numerous times a day. While it is very challenging to keep Band-Aid stickers to stay on skin for a week, conventional wearable patches normally have much stiffer rigid substrates, which make them more easily rubbed off than Band-Aid stickers. In addition, it is also very challenging to make a tag or a patch to be comfortable to the user. Ideally the patch needs to be stretchable, flexible, and breathable.

Figure 2:
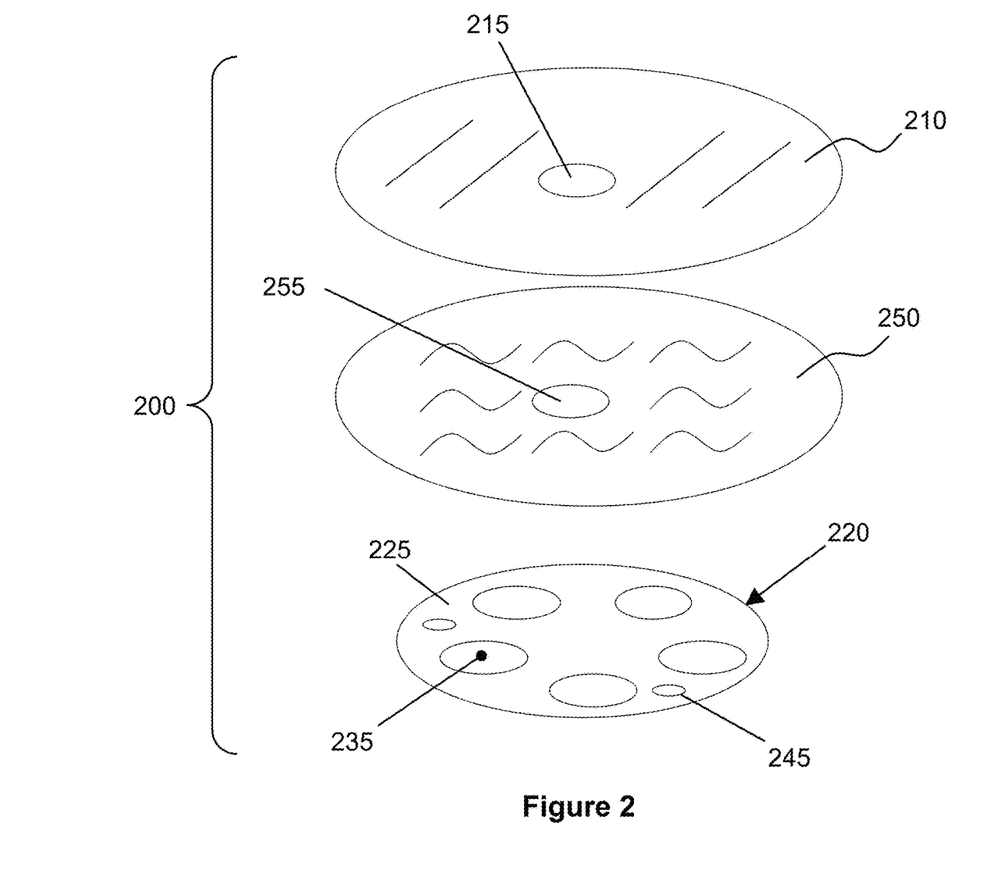
FIG. 2 is an exploded perspective view of an exemplified compliant wearable patch in accordance with some embodiments of the present invention.
Figure 3:
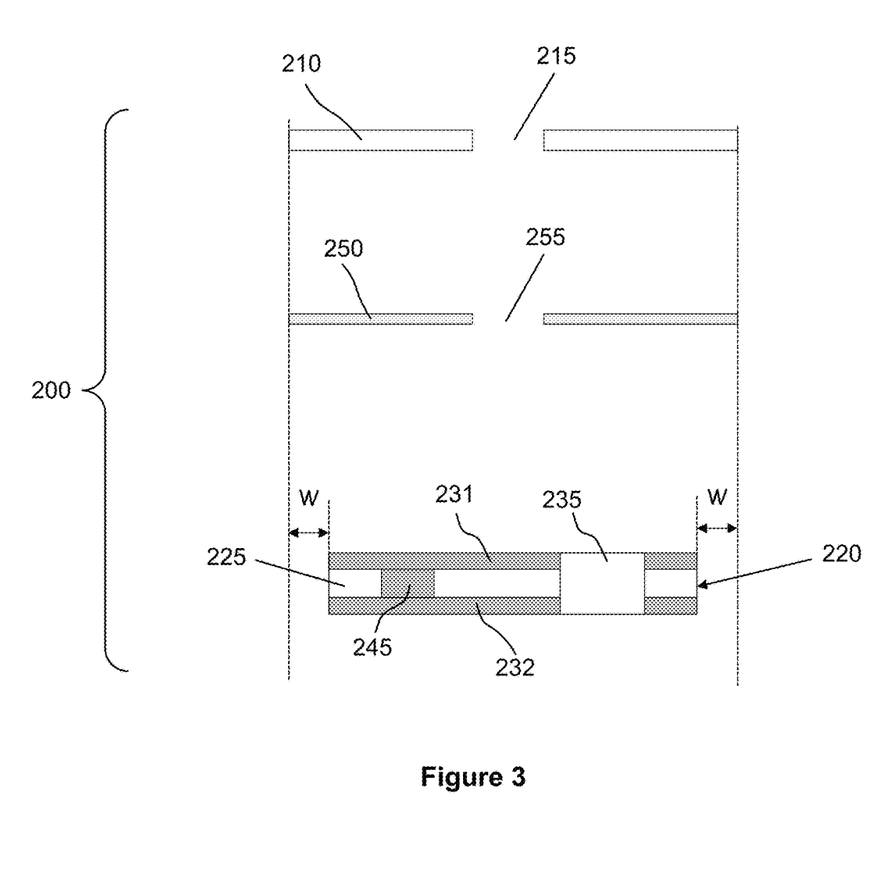
FIG. 3 is a cross-sectional view of an exemplified compliant wearable patch in accordance with some embodiments of the present invention.

The presently disclosure aims to overcome the drawbacks in the conventional electrode, and to provide highly compliant, flexible, and durable electrodes that are also comfortable for users to wear, with the potential of eliminating the requirements for conductive gel. Referring to FIGS. 2 and 3, a compliant wearable patch 200 includes an elastic layer 210, a shearable electrode layer 220, and an adhesive layer 250. The shearable electrode layer 220 includes a non-conductive support substrate 225, an upper electrode layer 231 on the non-conductive support substrate 225, a lower electrode layer 232 below the non-conductive support substrate 225, and via 245 that is conductively connected to the upper electrode layer 231 and the lower electrode layer 232. The lower electrode layer 232 is configured to be in contact with a user's skin and to pick up electrical signals from the user's body. The electrical signals are transmitted to the upper electrode layer 231 through the via 245. The elastic layer 210 and the adhesive layer 250 are chosen from ultra-compliant materials. Moisture and air can pass through the two layers easily so it brings good breathability to the skin. Optionally, the elastic layer 210 and the adhesive layer 250 can respectively include registered openings 215, 255 which expose an upper surface of the upper electrode layer 231 and allow an electrical lead to connect to the upper electrode layer 231 and to bring the electrical signal to external devices. The electrical lead from the electrode layers to the flexible electronic circuits can also be made on the same layer of flexible printed circuit/substrate and from the same manufacturing process as the upper electrode layer 231 and the lower electrode layer 232. In this case, the holes 255 and 215 are not required.

The elastic layer 210 and the adhesive layer 250 can be wider than the shearable electrode layer 220 by an edge clearance W. Thus when the compliant wearable patch 200 is placed onto a human body, a portion of the adhesive layer 250 can come to be contact with the human body to firmly hold the compliant wearable patch 200 to the skin. In some embodiments, the edge clearance W can be larger than 0.5 mm and less than 100 mm to ensure enough adhesion to the skin and still provide enough comfort to the user.

The support substrate 225 is rigid enough to support the upper electrode layer 231 and the lower electrode layer 232. In some embodiments, the support substrate 225 can have Young's Modulus larger than 0.5 Gpa, such as in a range between 1.0-10 Gpa. Examples of materials suitable for the substrate 225 include Polyimide, Polyester, Aramid, Glass epoxy, Silicone, Polyurethane, and Polyethylene naphalate. Importantly, the support substrate 225 is structured to provide stretchability to the shearable electrode layer 220. The support substrate 225 includes openings 235, which makes the shearable electrode layer 220 shearable and stretchable when the compliant wearable patch 200 is stretched or elongated. By strategically forming openings in the support substrate 225, the effective flexibility of the support substrate 225 is increased significantly (the effective elastic constant is decreased). In some embodiments, the support substrate 225 is thinner than 0.1 mm to allow flexibility (bendability), and effective elasticity of the support substrate 225 is strategically structured by openings. In some embodiments, the support substrate 225 is thicker than 0.001 mm to allow enough strength to support the upper electrode layer 231 and the lower electrode layer 232.

The elastic layer 210 can be made of a viscoelastic polymeric material having low Young's modulus and high failure strain. In some embodiments, the elastic layer 210 has Young's Modulus <0.3 Gpa. In some cases, the elastic layer 210 and can have Young's Modulus <0.1 Gpa to provide enhanced flexibility and tackability. Materials suitable for the elastic layer 210 include elastomers, viscoelastic polymers, such as silicone, and medical grade polyurethane that is a transparent medical dressing used to cover and protect wounds with breathability and conformation to skin.

Thus, the elastic layer 210 and the shearable electrode layer 220 provide support as well as compliance, stretchability, flexibility, breathability, and durability to the compliant wearable patch 200. The elastic layer 210 and the shearable electrode layer 220 are compliant and can conform to the skin under different moving positions, which can repeatedly elongate and compress the compliant wearable patch 200. The elastic layer 210 and the shearable electrode layer 220 are also breathable to allow aspiration and moisture from the skin to be released to the environment. The opening 235 in the middle of the shearable electrode layer 220 provides additional breathability to the electrode 200. The adhesive layer 250 can come into contact and adhere to the skin of a user through these openings 235 to secure the bonding of electrode to skin, which is critical for the consistent reliable data collection.

Figure 4:
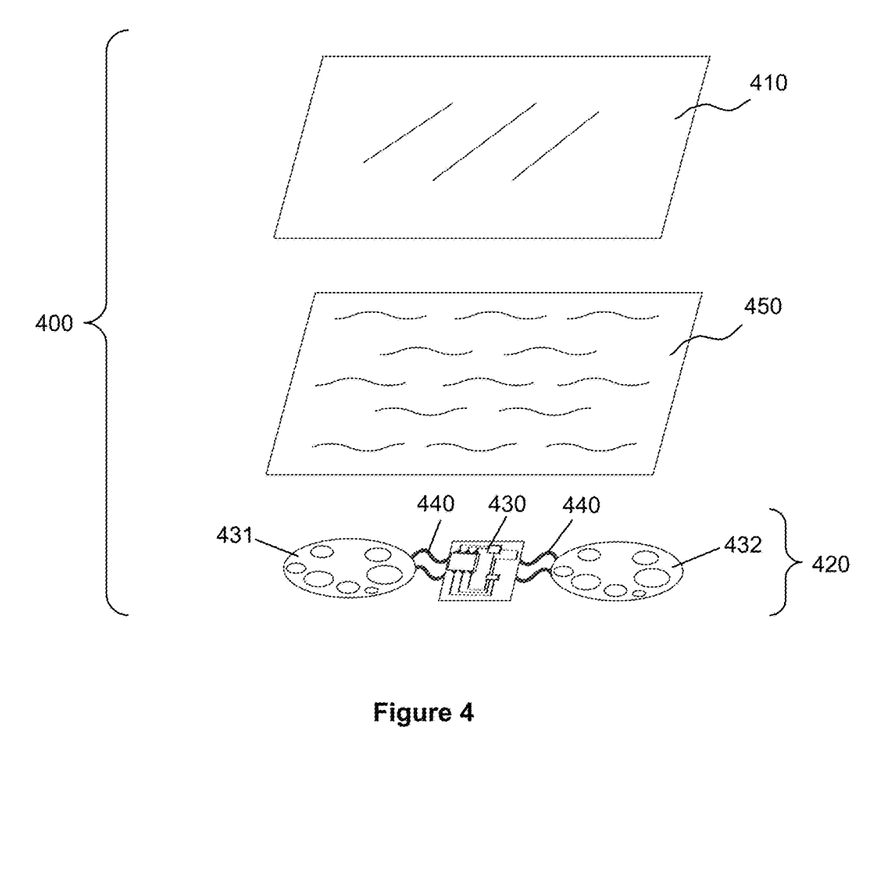
FIG. 4 is an exploded perspective view of another exemplified compliant wearable patch in accordance with some embodiments of the present invention.

In some embodiments, referring to FIG. 4, a compliant wearable patch 400 includes an elastic layer 410, an adhesive layer 450, and a shearable electrode layer 420. The shearable electrode layer 420 includes a network of circuit modules 430, 431, 432 connected by flexible ribbons 440 embedded with conductive lines. The flexible ribbons 440 can be made on the same flex layer as the circuit modules 430, 431 and 432 during the same manufacturing process of the circuits. The flexible ribbons 440 can also be a separate component made from a different process of the circuit modules 430, 431, and 432.

At least one circuit module 430 is configured to wirelessly communicate with external devices, based on wireless communication standards such as NFC standard, RFID, Wi-Fi, or Bluetooth. The circuit module 430 includes a support substrate, and one or multiple semiconductor chips, a circuit, and an antenna circuit formed on or in the support substrate. Examples of external devices include smart phones, computers, mobile payment devices, scanners and readers (e.g. RFID readers), medical devices, security systems, personal identification systems, etc. The antenna circuit can be compatible for NFC communications in a frequency range near 13.56 MHz, as described above, as well as UHF RFID at about 915 MHz, Bluetooth in 2.4 GHz or 5 GHz frequency ranges, and other types of wireless communications.

One or more of the circuit modules 431, 432 can have structures similar to the shearable electrode layer 220 as described above in relation to FIG. 2. The electrical signals picked up by the (lower) electrode layers in the circuit modules 431, 432 are transferred to the circuit module 430, which in turn can wirelessly transmit the electrical signals to an external device.

The flexible ribbon 440 can be in curly or serpentine shape, which allows stretchability when the compliant wearable patch 400 is stretched during wearing.

The elastic layer 410 is breathable to allow aspiration and moisture from the skin to be released to the environment. The network of circuit modules 430-432 and the flexible ribbons 440 define openings 535 in between to provide additional breathability to the compliant wearable patch 400. Furthermore, opening holes or voids can be made on the circuit modules 430-432 to increase its breathability and the effective elasticity. The support substrates in the circuit modules 430-432 can be contiguous to support the circuit modules 430-432 and the conductive lines in the flexible ribbons 440. In manufacturing, the support substrates in the circuit modules 430-432 can be formed in a single manufacturing step from a continuous sheet of material. The openings between the circuit modules 430-432 and the flexible ribbons 440 can be formed cutting a continuous sheet by techniques such as laser cutting and/or die cutting. It should be noted that the presently disclosed "single substrate" structure for the circuit layer is drastically different from conventional approaches, where different rigid boards/modules are connected with flexible ribbons via connectors. In our proposed approach, the modules and ribbons are made on one single continuous substrate. Openings or voids are created on the substrate to provide high effective elasticity and breathability.

Similar to the elastic layer 210 (FIGS. 2 and 3), the elastic layer 410 can be selected from a material that has low Young's modulus and high failure strain, for example, a viscoelastic polymeric material. In some embodiments, the elastic layer 410 has Young's Modulus <0.3 Gpa. In some cases, the elastic layer 410 and can have Young's Modulus <0.1 Gpa to provide enhanced flexibility and tackability. Materials suitable for the elastic layer 410 include elastomers, viscoelastic polymers, such as silicone, and medical grade polyurethane that is a transparent medical dressing used to cover and protect wounds with breathability and conformation to skin. In some embodiments, the support substrate 410 is thinner than 0.5 mm.

The support substrates in the circuit modules 430-432 are rigid enough to support the upper electrode layer and the lower electrode layer 232, or the conductive circuit and semiconductor chip. In some embodiments, the support substrates have Young's Modulus larger than 0.5 Gpa, such as in a range between 1.0-10 Gpa. Examples of materials suitable for the substrates include Polyimide, polyester, Aramid, Composite, Glass epoxy, silicone, polyurethane, and Polyethylene naphalate.

Figure 5:
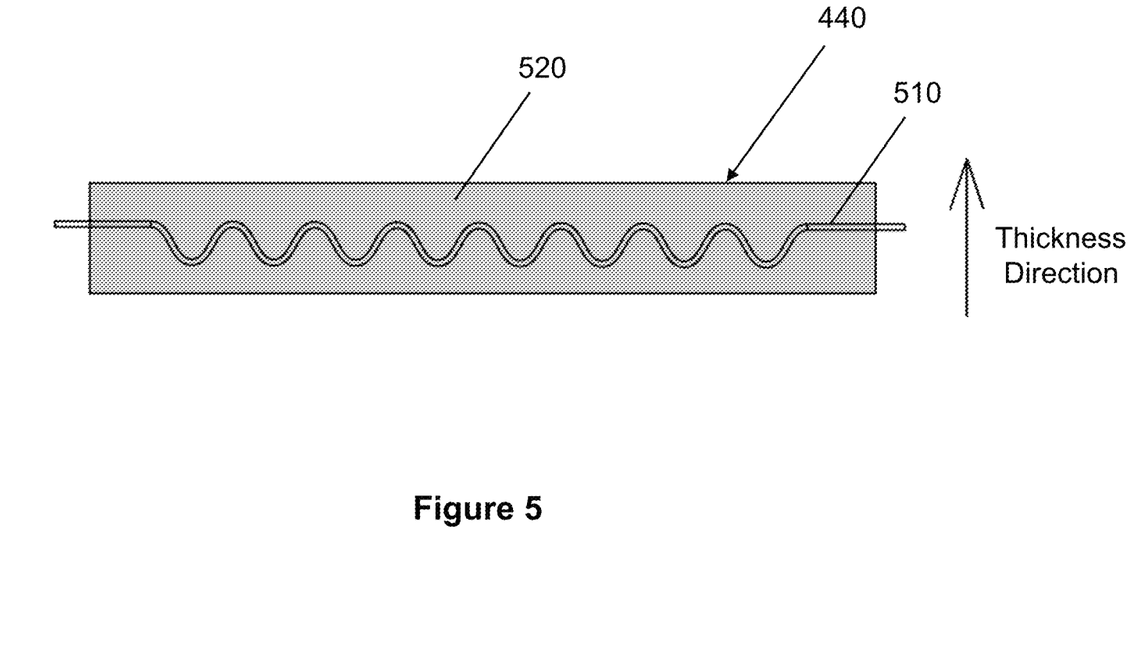
FIG. 5 is a cross-sectional view of a flexible ribbon for connecting circuit modules in accordance with some embodiments of the present invention.

The flexible ribbons 440 can also include a zigzag structure as shown in FIG. 5. The flexible ribbon 440 includes a conductive trace layer 510 optionally with a supporting substrate layer that is sealed in an elastomer matrix 520 (i.e. a polymer matrix). The conductive trace layer 510 is zigzagged in a direction normal to the skin of the wearer or the thickness direction of the compliant wearable patch 400. The conductive trace layer 510 is embedded in the elastomer matrix 520 and is configured to connect the conductive circuit in the circuit module 430 and the upper electrode layer the second circuit module 431, 432 (FIG. 4). The elastomer matrix 520 can deform easily with high strain under low stretch force. With the zigzag structure, the flexible ribbon 440 can be stretched with movement of skin with least constraints.

Figure 6:
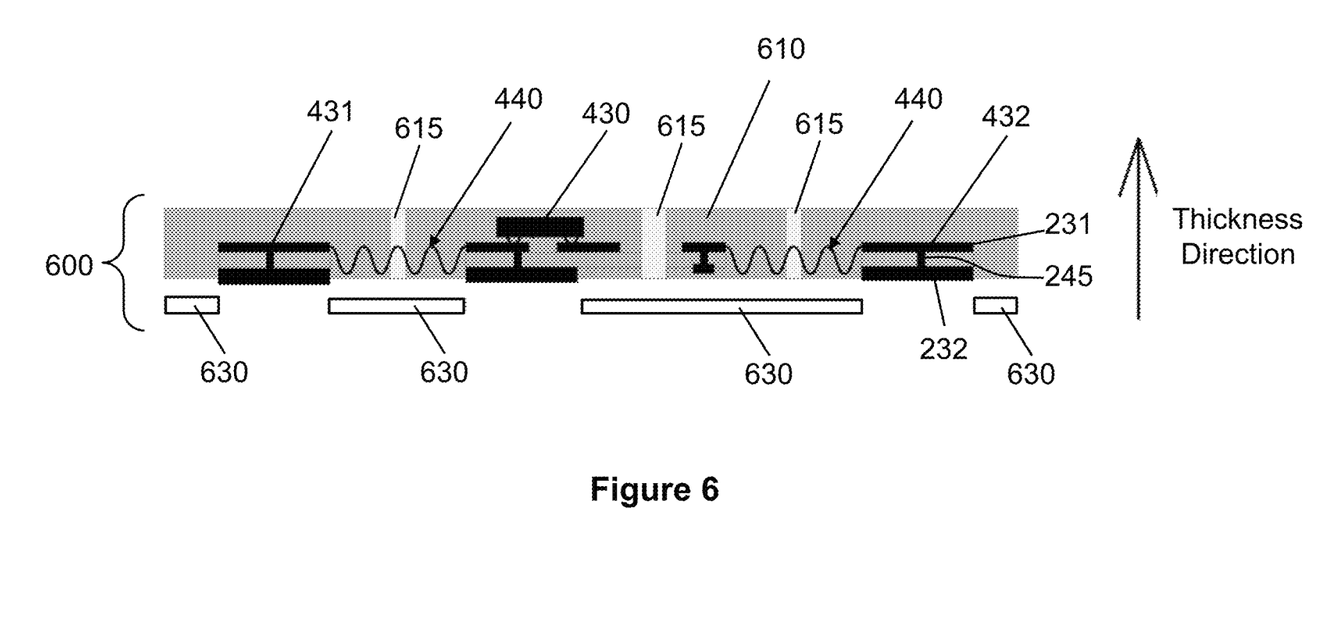
FIG. 6 is a cross-sectional view of an exemplified compliant wearable patch in accordance with some embodiments of the present invention.

Referring to FIG. 6, a compliant wearable patch 600 includes circuit modules 430-432 which are connected by flexible ribbons 440. The circuit modules 430-432 and the flexible ribbons 440 are molded in an elastomer polymer matrix 610. The flexible ribbons 440 include connecting lines configured to transmit the electrical signal from the upper electrode layer 231 to the circuit module 430. The circuit module 430, 431 and 432 can include openings as shown in FIG. 6 and described above. The flexible ribbons 440 can have a curly or serpentine shape (shown in FIG. 4) or zigzag shape in thickness direction (shown in FIG. 5). The openings, the shapes of the flexible ribbons 440 and the elastomer polymer matrix 610 enable the shearable electrode layer 420 and the compliant wearable patch to deform easily in the compliant elastomer matrix according to skin deformation with least stress constraints. The compliant matrix material can be formed by a very soft material and can be selected from elastomer materials, such as silicone, polyurethane and other elastomer materials. Multiple opening 615 can be made through the elastomer polymer matrix 610 to give more breathability for skin. The elastomer polymer matrix 610 can also protect chips and circuits from external mechanical damage or electronic discharge to improve reliability in complex environment. The upper electrodes 231 are embedded in the elastomer polymer matrix 610 whereas the lower electrodes 232 have their lower surfaces exposed so they can be in contact with the skin. The upper electrodes 231 and the lower electrodes 232 are conductively connected by vias 245. A pressure sensitive adhesive layer 630 is formed on the lower surface of the elastomer polymer matrix 610 but outside the areas of the lower electrode 232. The adhesive layer 630 can be laminated to the elastomer polymer matrix 610 for good binding to skin. In this case, the elastomer polymer matrix 610 can remove the need for an elastic layer (like 410 (in FIG. 4).

Details about a network of circuit modules in a wearable patch are disclosed in commonly assigned pending U.S. patent application Ser. No. 14/491,665, titled "highly compliant wearable wireless patch having stress-relief capability", filed on Sep. 19, 2014, the disclosure of which is incorporated herein by reference.

Details about a network of circuit modules in a wearable patch are also disclosed in commonly assigned pending U.S. patent application Ser. No. 14/454,457, titled "Stretchable multi-layer wearable tag capable of wireless communications", filed on Aug. 7, 2014, the disclosure of which is incorporated herein by reference.

An advantage of the disclosed compliant wearable patch is its mechanical robustness comparing with conventional wearable patches. The latter has high rigidity and sometimes easy to fracture or delaminate. The shearable electrode layer is structured to be shearable and compliant; the elastic layers are made of materials such as a polymer material such as an elastomer, which together makes the wearable patches highly compliant, stretchable, and flexible. The elastic layers and the support substrate can reduce the impact of rubbing force on the rigid dry inlay layer underneath, which provides better protection to the semiconductor chip and the antenna circuit. The compliant wearable patches are thus resilient to starching and compressing during wearer's body movement. Thus, the elastic layers and the support substrate can reduce the probability of falling off, thus increasing the life span of the compliant wearable patch.

The adhesive layer can be pressure sensitive, which allows the compliant wearable patches tightly adhere to human skin under pressure, applied for example by a thumb. For instance, the adhesive layer can be made of a medical pressure sensitive adhesive. An example of such adhesive is medical grade tackified Hypoallergenic Pressure Sensitive Adhesive.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Only a few examples and implementations are described. Other implementations, variations, modifications and enhancements to the described examples and implementations may be made without deviating from the spirit of the present invention. For example, the usages of the disclosed wearable patches are not limited by the examples given above; they can be applicable to many other fields. The materials suitable for the different layers of the wearable patches are also not limited by the examples provided. The layouts and forms of the elastic layer, the compliant strap layers, the breathing openings, the decorative pattern, the semiconductor chip, the antenna, the metal pads, and the connection leads can have other configurations without deviating from the present invention.

What is claimed is:
1. A wearable patch, comprising:
an elastic layer;
an adhesive layer under the elastic layer; and a shearable electrode layer under the adhesive layer, comprising:
  a support substrate;
  an upper electrode layer on the support substrate; and
  a lower electrode layer under the support substrate, wherein the support substrate includes a via that is conductively connected to the upper electrode layer and the lower electrode layer,
  wherein the shearable electrode layer comprises one or more openings through the support substrate, the upper electrode layer, and the lower electrode layer to allow the shearable electrode layer to be sheared and elongated, and breathable,
  wherein the lower electrode layer is configured to be in contact with a user's body and to pick up electric signals from the user's body.

2. The wearable patch of claim 1, wherein the elastic layer and the adhesive layer respectively include registered openings, which expose an upper surface of the upper electrode layer.

3. The wearable patch of claim 2, wherein the registered openings are configured to allow an electric lead to connect the upper electrode layer to an external device.

4. The wearable patch of claim 1, wherein the elastic layer and the adhesive layer are wider than the shearable electrode layer.

5. The wearable patch of claim 4, wherein the elastic layer and the adhesive layer are wider than the shearable electrode layer by an edge clearance along an edge, wherein the edge clearance has a width between 0.5 mm and 100 mm.

6. The wearable patch of claim 1, wherein the support substrate has a Young's Modulus higher than 0.5 Gpa.

7. The wearable patch of claim 1, wherein the support substrate is thinner than 1.0 mm.

8. The wearable patch of claim 1, wherein the elastic layer has a Young's Modulus lower than 0.3 Gpa.

9. A wearable patch capable of wireless communications, comprising:
  an elastic layer;
  an adhesive layer under the elastic layer; and
  a shearable electrode layer under the adhesive layer, comprising:
    a first circuit module comprising:
      a first support substrate;
      a conductive circuit embedded in the first support substrate; and
      a semiconductor chip in connection with the conductive circuit; and
    a second circuit module comprising:
      a second support substrate;
      an upper electrode layer on the second support substrate; and
      a lower electrode layer under the second support substrate, wherein the second support substrate includes a via that is conductively connected to the upper electrode layer and the lower electrode layer, wherein the second circuit module comprises one or more openings through the second support substrate, the upper electrode layer, and the lower electrode layer to allow the shearable electrode layer to be sheared and elongated, and breathable,
      wherein the lower electrode is configured to be in contact with a user's body and to pick up electrical signals from the user's body; and
    a flexible ribbon that connect the first support substrate in the first circuit module and the second support substrate in the second circuit module, wherein the flexible ribbon is embedded with a connecting line configured to transmit the electrical signals from the upper electrode layer to the first circuit module.

10. The wearable patch of claim 9, wherein the first circuit module is configured to receive or transmit wireless signals in communications with an external device.

11. The wearable patch of claim 10, wherein the conductive circuit includes an antenna circuit configured to receive or transmit wireless signals in communications with an external device.

12. The wearable patch of claim 10, wherein the first circuit module is configured to wirelessly communicate with the external device based on near field communication (NFC), Wi-Fi, Bluetooth, or RFID wireless communication standard.

13. The wearable patch of claim 9, wherein the second support substrate has a Young's Modulus higher than 0.5 Gpa.

14. The wearable patch of claim 9, wherein the second support substrate is thinner than 0.5 mm.

15. The wearable patch of claim 9, wherein the elastic layer has a Young's Modulus lower than 0.3 Gpa.

16. The wearable patch of claim 9, the flexible ribbon comprises:
  a polymer matrix; and
  a conductive trace layer embedded in the polymer matrix, wherein the conductive trace layer has a zigzag structure, wherein the conductive trace layer is configured to connect the conductive circuit in the first circuit module and the upper electrode layer in the second circuit module.

* * * * *